US012188064B2

(12) United States Patent
Friis et al.

(10) Patent No.: US 12,188,064 B2
(45) Date of Patent: Jan. 7, 2025

(54) SUBTILASE VARIANTS AND COMPOSITIONS COMPRISING SAME

(71) Applicant: NOVOZYMES A/S, Bagsvaerd (DK)

(72) Inventors: Esben Peter Friis, Herlev (DK); Rolf Thomas Lenhard, Lyngby (DK); Lars Lehmann Hylling Christensen, Alleroed (DK); Carl Mikael Bauer, Malmoe (SE)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 17/040,207

(22) PCT Filed: Mar. 21, 2019

(86) PCT No.: PCT/EP2019/057024
§ 371 (c)(1),
(2) Date: Sep. 22, 2020

(87) PCT Pub. No.: WO2019/180111
PCT Pub. Date: Sep. 26, 2019

(65) Prior Publication Data
US 2021/0009979 A1   Jan. 14, 2021

(30) Foreign Application Priority Data
Mar. 23, 2018  (EP) .................. 18163651

(51) Int. Cl.
*C12N 9/54* (2006.01)
*C11D 3/386* (2006.01)

(52) U.S. Cl.
CPC ............ *C12N 9/54* (2013.01); *C11D 3/38618* (2013.01); *C11D 3/38663* (2013.01); *C12Y 304/21062* (2013.01)

(58) Field of Classification Search
None
See application file for complete search history.

(56) References Cited

U.S. PATENT DOCUMENTS

| | | | | |
|---|---|---|---|---|
| 6,312,936 B1 * | 11/2001 | Poulose | ............. | C11D 3/38618 |
| | | | | 435/219 |
| 6,440,717 B1 * | 8/2002 | Brode, III | .......... | C11D 3/38609 |
| | | | | 435/222 |
| 2003/0157645 A1 | 8/2003 | Kettling | | |
| 2017/0305963 A1 | 10/2017 | Quaedflieg | | |

FOREIGN PATENT DOCUMENTS

| | | |
|---|---|---|
| EP | 1321513 A1 | 6/2003 |
| WO | 8909830 A1 | 10/1989 |
| WO | 9530010 A1 | 11/1995 |

OTHER PUBLICATIONS

Guo et al, Protein tolerance to random amino acid change. Proc Natl Acad Sci U S A. Jun. 22, 2004;101(25):9205-9210. Epub Jun. 14, 2004.*
Orna Almog et al, 2002, J Biol Chem 277(30), 27553-27558.
WO 2016-056913—EBI Accession No. LQ338923.
WO 2003-054127—EBI Accession No. AX799040.

* cited by examiner

*Primary Examiner* — Richard G Hutson
(74) *Attorney, Agent, or Firm* — Kelly K. Reynolds

(57) ABSTRACT

The invention relates to subtilase variants and detergent compositions comprising the variants, as well as methods of producing the variants and methods for stabilizing a subtilase variant.

10 Claims, No Drawings
Specification includes a Sequence Listing.

SEQUENCE LISTING

```
<160> NUMBER OF SEQ ID NOS: 1

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275
```

SUBTILASE VARIANTS AND COMPOSITIONS COMPRISING SAME

CROSS-REFERENCE TO RELATED APPLICATIONS

This application is a 35 U.S.C. 371 national application of international application no. PCT/EP2019/057024 filed Mar. 21, 2019, which claims priority or the benefit under 35 U.S.C. 119 of European application no. 18163651.5 Mar. 23, 2018, the contents of which are fully incorporated herein by reference.

REFERENCE TO A SEQUENCE LISTING

This application contains a sequence listing in computer readable form, which is incorporated herein by reference.

FIELD OF THE INVENTION

The present invention relates to subtilase variants, compositions comprising the variants, polynucleotides encoding the variants, methods of producing the variants, and methods of using the variants.

BACKGROUND OF THE INVENTION

Subtilisins are serine proteases from the family S8, in particular from the subfamily S8A, as defined by the MEROPS database (world wide web address_ebi.ac.uk/merops/index.shtml). In subfamily S8A the key active site residues Asp, His and Ser are typically found in motifs that differ from those of the S8B subfamily. Subtilisin BPN' (also known under the acronym BASBPN) from *Bacillus amyloliquefaciens* has the MEROPS numbers S08.034 and is a member of the S8A subfamily.

In the detergent industry, enzymes have for many decades been implemented in washing formulations. Enzymes used in such formulations comprise proteases, lipases, amylases, cellulases, mannosidases as well as other enzymes or mixtures thereof. Commercially, the most important enzymes are proteases.

An increasing number of commercially used proteases for e.g. laundry and dishwashing detergents are protein engineered variants of naturally occurring wild type proteases, Further, other subtilase variants have been described in the art with alterations relative to a parent subtilase resulting in improvements such as better wash performance, thermal stability, storage stability or catalytic activity.

However, various factors make further improvement of proteases advantageous. For example, washing conditions such as temperature and pH tend to change over time, and are also different in different countries or regions of the world, and many stains are still difficult to completely remove under conventional washing conditions. Another challenge in detergent compositions is enzyme stability, since the chemical components of these compositions as well as conditions of pH, temperature and humidity often tend to inactivate enzymes. Further, in-wash conditions can also result in inactivation of the enzymes (due to e.g. pH, temperature or chelation instability), resulting in loss of wash performance during the wash cycle. Thus, despite the intensive research in protease development there remains a need for new and improved proteases that have improved stability, for example improved storage stability, e.g. in a detergent composition, and which at the same time have similar or improved wash performance compared to the parent subtilase.

The present invention addresses these challenges by providing subtilase variants with improved stability.

SUMMARY OF THE INVENTION

The present invention relates to subtilase variants, comprising an alteration at two, three or more positions, e.g. four or more positions, corresponding to positions 9, 63, 76, 88, 104, 107, 128, 131, 159, 204, 206, 209, 212, 215, 216, 261 and 262 of the polypeptide of SEQ ID NO: 1, wherein the variants have subtilase activity.

The present invention also relates to compositions comprising the variants, in particular detergent compositions, polynucleotides encoding the variants; nucleic acid constructs, vectors, and host cells comprising the polynucleotides; and methods of producing the variants.

The present invention further relates to methods for stabilizing a subtilase variant and for producing a subtilase variant.

DEFINITIONS

Subtilase/protease: The terms "subtilase" and "protease" may be used interchangeably herein and refer to an enzyme that hydrolyses peptide bonds in proteins. This includes any enzyme belonging to the EC 3.4 enzyme group (including each of the thirteen subclasses thereof), and in particular endopeptidases (EC 3.4.21). The EC number refers to Enzyme Nomenclature 1992 from NC-IUBMB, Academic Press, San Diego, California, including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively.

Protease activity: The term "protease activity" means a proteolytic activity (EC 3.4), in particular endopeptidase activity (EC 3.4.21). There are several protease activity types, the three main activity types being: trypsin-like, where there is cleavage of amide substrates following Arg or Lys at P1, chymotrypsin-like, where cleavage occurs following one of the hydrophobic amino acids at P1, and elastase-like with cleavage following an Ala at P1. For purposes of the present invention, protease activity is determined according to the procedure described in "Materials and Methods" below. The subtilisin variants of the present invention preferably have at least 50%, e.g. at least 60%, at least 70%, at least 80%, at least 90%, at least 95% or at least 100% of the protease activity of the polypeptide of SEQ ID NO: 1.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial primary RNA transcript is a precursor to mRNA that is processed through a series of steps, including splicing, before appearing as mature spliced mRNA.

Coding sequence: The term "coding sequence" means a polynucleotide which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more amino acids absent from the amino and/or carboxyl terminus of a mature polypeptide; wherein the fragment has subtilase activity. Such a fragment preferably contains at least 85%, at least 90% or at least 95% of the number of amino acids in SEQ ID NO: 1.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent protease or the protease with SEQ ID NO: 1. Such improved properties include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity and thermostability. In a preferred aspect of the present invention, the improved property is improved stability, in particular improved storage stability in a detergent formulation, where the storage stability may be determined based on culture supernatants or on purified proteases, e.g. as described in the examples herein.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having subtilase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent subtilase/protease: The term "parent" or "parent subtilase" or "parent protease" means any polypeptide with subtilase activity to which an alteration is made to produce the enzyme variants of the present invention. The parent may be a naturally occurring (wild-type) polypeptide or a variant thereof of a wild-type polypeptide. In a particular embodiment, the parent is a protease with at least 75% identity, such as at least 80%, at least 85%, at least 90%, at least 91%, at least 92%, at least 93%, at least 94%, at least 95%, at least 96%, at least 97%, at least 98% or at least 99% identity with SEQ ID NO: 1. Alternatively, the parent may have 100% identity to SEQ ID NO: 1.

Sequence identity: The relatedness between two amino acid sequences or between two nucleotide sequences is described by the parameter "sequence identity.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment− Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having subtilase activity comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position.

Wild-type subtilase: The term "wild-type" subtilase means a subtilase expressed by a naturally occurring microorganism, such as a bacterium, yeast, or filamentous fungus found in nature. An example of a wild-type subtilase is subtilisin BPN', i.e., amino acids 1 to 275 of SEQ ID NO: 1.

Conventions for Designation of Variants

For purposes of the present invention, the polypeptide with SEQ ID NO: 1 is used to determine the corresponding amino acid residue in another subtilase. The amino acid sequence of another subtilase is aligned with the polypeptide disclosed in SEQ ID NO: 1, and based on the alignment, the amino acid position number corresponding to any amino acid residue in the polypeptide of SEQ ID NO: 1 is determined using the Needleman-Wunsch algorithm as described above under "Sequence identity" and with the parameters described above.

Identification of the corresponding amino acid residue in another subtilase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

In describing the variants of the present invention, the nomenclature described below is adapted for ease of reference. The accepted IUPAC single letter or three letter amino acid abbreviation is employed. The terms "alteration" or "mutation" may be used interchangeably herein to refer to substitutions, insertions and deletions.

Substitutions. For an amino acid substitution, the following nomenclature is used: Original amino acid, position, substituted amino acid. Accordingly, the substitution of a threonine at position 220 with alanine is designated as "Thr220Ala" or "T220A". Multiple substitutions may be separated by addition marks ("+"), e.g., "Thr220Ala+Gly229Val" or "T220A+G229V", representing substitutions at positions 220 and 229 of threonine (T) with alanine (A) and glycine (G) with valine (V), respectively. Multiple substitutions may alternatively be listed with individual mutations separated by a space or a comma. Alternative substitutions in a particular position may be indicated with a slash ("/"). For example, substitution of threonine in position 220 with either alanine, valine or leucine many be designated "T220A/V/L".

Deletions. For an amino acid deletion, the following nomenclature is used: Original amino acid, position, *. Accordingly, the deletion of threonine at position 220 is designated as "Thr220*" or "T220*". Multiple deletions may be separated by addition marks ("+"), e.g., "Thr220*+Gly229*" or "T220*+G229*", or alternatively may be separated by a space or comma.

Insertions. For an amino acid insertion, the following nomenclature is used: Original amino acid, position, original amino acid, inserted amino acid. Accordingly, the insertion of lysine after threonine at position 220 is designated "Thr220ThrLys" or "T220TK". An insertion of multiple amino acids is designated [Original amino acid, position, original amino acid, inserted amino acid #1, inserted amino acid #2; etc.]. For example, the insertion of lysine and alanine after threonine at position 220 is indicated as "Thr220ThrLysAla" or "T220TKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 220     | 220 220a 220b |
| T       | T - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Multiple alterations may alternatively be listed with individual mutations separated by a space or a comma.

Different alterations. Where different alterations can be introduced at a position, the different alterations may be separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Different alterations in a position may also be indicated with a slash ("/"), for example "T220A/V/L" as explained above. Alternatively, different alterations may be indicated using brackets, e.g., Arg170[Tyr, Gly] or in one-letter code R170 [Y,G].

DETAILED DESCRIPTION OF THE INVENTION

The present invention relates to subtilase variants comprising mutations at three or more positions, e.g. four or more positions, selected from 9, 63, 76, 88, 104, 107, 128, 131, 159, 204, 206, 209, 212, 215, 216, 261 and 262, wherein positions are numbered according to SEQ ID NO: 1, and wherein the variant has protease activity and a sequence identity to SEQ ID NO: 1 of at least 80% and less than 100%.

Variants

In one embodiment, the invention provides a subtilase variant comprising mutations at three or more positions, e.g. four or more positions, selected from:
- (i) 209 in combination with two or more mutations at positions selected from 63, 215 and 217;
- (ii) 104 and 128 in combination with at least one mutation at a position selected from 9, 63, 76, 107, 131, 159, 204, 206, 212, 215, 216 and 217;
- (iii) 9 in combination with at least two mutations at positions selected from 76, 204 and 212;
- (iv) 76 in combination with at least two mutations at positions selected from 9, 88, 159, 204, 206, 212, 216, 261 and 262;
- (v) 206 in combination with at least two mutations at positions selected from 9, 76, 159, 204, 209, 212, 216, 217, 261 and 262; and
- (vi) 204, 212 and 216, preferably in combination with at least one mutation at a position selected from 9, 159 and 206;

wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%.

In some embodiments, the mutations in positions 9, 63, 76, 88, 104, 107, 128, 131, 159, 204, 206, 209, 212, 215, 216, 261 and 262 are selected from the following:
- the mutation in position 9 is S9E or S9D, preferably S9E;
- the mutation in position 63 is S63G or S63A, preferably S63G;
- the mutation in position 76 is N76D or N76E, preferably N76D;
- the mutation in position 88 is A88V, A88I, A88L or A88M, preferably A88V;
- the mutation in position 104 is Y104V, Y104I, Y104L or Y104M, preferably Y104V;
- the mutation in position 107 is I107L, I107V, I107M, preferably I107L;
- the mutation in position 128 is G128S, G128A or G128T, preferably G128S;
- the mutation in position 131 is G131* or G131P;
- the mutation in position 159 is S159E or S159D, preferably S159E;
- the mutation in position 204 is S204D or S204E, preferably S204D;
- the mutation in position 206 is Q206L, Q206I, Q206V or Q206M, preferably Q206L;
- the mutation in position 209 is L209W;
- the mutation in position 212 is N212G, N212A or N212S, preferably N212G;
- the mutation in position 215 is G215A;
- the mutation in position 216 is A216V, A216I, A216L or A216M, preferably A216V;
- the mutation in position 217 is Y217L, Y217I, Y217V or Y217M, preferably Y217L;
- the mutation in position 261 is F261W, F261N or F261Y, preferably F261W; and/or
- the mutation in position 262 is Y262E or Y262D, preferably Y262E.

In another embodiment, the invention provides a subtilase variant comprising three or more mutations, e.g. four or more mutations, selected from:
- (i) L209W in combination with two or more substitutions selected from S63G/A, G215A and Y217L/I/V/M;
- (ii) Y104V/I/L/M and G128S/A/T in combination with at least one mutation selected from S9E/D, S63G/A, N76D/E, I107L/V/M, G131*, G131P, S159E/D, S204D/E, Q206L/I/V/M, N212G/A/S, G215A, A216V/I/L/M and Y217L/I/V/M;
- (iii) S9E/D in combination with at least two substitutions selected from N76D/E, S204D/E and N212G/A/S;
- (iv) N76D/E in combination with at least two substitutions selected from S9E/D, A88V/I/L/M, S159E/D, S204D/E, Q206L/I/V/M, N212G/A/S, A216V/I/L/M, F261W/N/Y and Y262E/D;
- (v) Q206L/I/V/M in combination with at least two substitutions selected from S9E/D, N76D/E, S159E/D, S204D/E, L209W/N/Y, N212G/A/S, A216V/I/L/M, Y217L/I/V/M, F261W/N/Y and Y262E/D; and
- (vi) S204D/E, N212G/A/S and A216V/I/L/M, preferably in combination with at least one substitution selected from S9E/D, S159E/D and Q206L/I/V/M;

wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%.

In a first aspect of the invention, the subtilase variant comprises or consists of the substitution L209W and at least two substitutions selected from the group consisting of S63G/A, G215A and Y217L/I/V/M, wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%.

The substitution in position 63 is preferably S63G, the substitution in position 215 is preferably G215A, and the substitution in position 217 is preferably Y217L. In a preferred embodiment, the subtilase variant of this aspect comprises each of the substitutions S63G, L209W, G215A and Y217L.

The subtilase variant of this aspect, comprising the substitution L209W and at least two substitutions selected from the group consisting of S63G/A, G215A and Y217L/I/V/M, wherein the substitution in position 63 preferably is S63G, the substitution in position 215 preferably is G215A and the substitution in position 217 preferably is Y217L, may further comprise at least one mutation, for example two, three or more mutations, selected from the group consisting of S9E/D, N76D/E, Y104V/I/L/M, G128S/A/T, G131*, G131P, S204D/E, Q206L/I/V/M, A216V/I/L/M, F261W/N/Y and Y262E/D.

In one embodiment, the subtilase variant comprises the substitutions S63G/A, L209W, G215A and Y217L/I/V/M, preferably S63G, L209W, G215A and Y217L, and further comprises a substitution in position 9 selected from S9E and S9D, preferably S9E.

In another embodiment, the subtilase variant comprises the substitutions S63G/A, L209W, G215A and Y217L/I/V/M, preferably S63G, L209W, G215A and Y217L, and further comprises a substitution in position 76 selected from N76D and N76E, preferably N76E.

In another embodiment, the subtilase variant comprises the substitutions S63G/A, L209W, G215A and Y217L/I/V/M, preferably S63G, L209W, G215A and Y217L, and further comprises a substitution in position 104 selected from Y104V, Y104I, Y104L and Y104M, preferably Y104V.

In another embodiment, the subtilase variant comprises the substitutions S63G/A, L209W, G215A and Y217L/I/V/M, preferably S63G, L209W, G215A and Y217L, and further comprises a substitution in position 128 selected from G128S, G128A and G128T, preferably G128S.

In another embodiment, the subtilase variant comprises the substitutions S63G/A, L209W, G215A and Y217L/I/V/M, preferably S63G, L209W, G215A and Y217L, and further comprises an alteration in position 131, wherein the alteration is selected from G131* and G131P.

In another embodiment, the subtilase variant comprises the substitutions S63G/A, L209W, G215A and Y217L/I/V/M, preferably S63G, L209W, G215A and Y217L, and further comprises a substitution in position 204 selected from S204D and S204E, preferably S204D.

In another embodiment, the subtilase variant comprises the substitutions S63G/A, L209W, G215A and Y217L/I/V/M, preferably S63G, L209W, G215A and Y217L, and further comprises a substitution in position 206 selected from Q206L, Q206I, Q206V and Q206M, preferably Q206L.

In another embodiment, the subtilase variant comprises the substitutions S63G/A, L209W, G215A and Y217L/I/V/M, preferably S63G, L209W, G215A and Y217L, and further comprises a substitution in position 216 selected from A216V, A216I, A216L and A216M, preferably A216V.

In another embodiment, the subtilase variant comprises the substitutions S63G/A, L209W, G215A and Y217L/I/V/M, preferably S63G, L209W, G215A and Y217L, and further comprises a substitution in position 261 selected from F261W, F261N and F261Y, preferably F261W.

In another embodiment, the subtilase variant comprises the substitutions S63G/A, L209W, G215A and Y217L/I/V/M, preferably S63G, L209W, G215A and Y217L, and further comprises a substitution in position 262 selected from Y262E and Y262D, preferably Y262E.

In another embodiment, the subtilase variant comprises the substitution S63G/A, L209W, G215A and Y217L/I/V/M, preferably S63G, L209W, G215A and Y217L, and further comprises a substitution in position 206 selected from selected from Q206L, Q206I, Q206V and Q206M, preferably Q206L, and a substitution in position 216 selected from A216V, A216I, A216L and A216M, preferably A216V.

In another embodiment, the subtilase variant comprises the substitution S63G/A, L209W, G215A and Y217L/I/V/M, preferably S63G, L209W, G215A and Y217L, and further comprises a substitution in position 261 selected from F261W, F261N and F261Y, preferably F261W, and a substitution in position 262 selected from Y262E and Y262D, preferably Y262E.

In another embodiment, the subtilase variant comprises the substitution S63G/A, L209W, G215A and Y217L/I/V/M, preferably S63G, L209W, G215A and Y217L, and further comprises a substitution in position 104 selected from Y104V, Y104I, Y104L and Y104M, preferably Y104V, and a substitution in position 128 selected from G128S, G128A and G128T, preferably G128S.

In another embodiment, the subtilase variant comprises the substitution S63G/A, L209W, G215A and Y217L/I/V/M, preferably S63G, L209W, G215A and Y217L, and further comprises a substitution in position 104 selected from Y104V, Y104I, Y104L and Y104M, preferably Y104V, a substitution in position 128 selected from G128S, G128A and G128T, preferably G128S, and an alteration in position 131, wherein the alteration is selected from G131* and G131P.

In a particular embodiment of this aspect of the invention, the subtilase variant comprises or consists of the set of mutations S63G L209W G215A Y217L.

In another particular embodiment, the subtilase variant comprises or consists of the set of mutations S9E S63G L209W G215A Y217L.

In another particular embodiment, the subtilase variant comprises or consists of the set of mutations S63G N76D L209W G215A Y217L.

In another particular embodiment, the subtilase variant comprises or consists of the set of mutations S63G S204D L209W G215A Y217L.

In another particular embodiment, the subtilase variant comprises or consists of the set of mutations S63G Q206L L209W G215A A216V Y217L.

In another particular embodiment, the subtilase variant comprises or consists of the set of mutations S63G Q206L L209W G215A Y217L.

In another particular embodiment, the subtilase variant comprises or consists of the set of mutations S63G L209W G215A Y217L F261W Y262E.

In another particular embodiment, the subtilase variant comprises or consists of the set of mutations S63G Y104V G128S G131* L209W G215A Y217L.

In another particular embodiment, the subtilase variant comprises or consists of the set of mutations S63G Y104V G128S G131P L209W G215A Y217L.

In a second aspect of the invention, the subtilase variant comprises or consists of the substitutions Y104V/I/L/M+G128S/A/T, preferably Y104V+G128S, and (a) at least two mutations selected from the group consisting of S9E/D, N76D/E, I107L/V/M, G131*, G131P, S159E/D, S204D/E, Q206L/I/V/M, N212G/A/S and A216V/I/L/M, or (b) L209W and at least two substitutions selected from the group consisting of S63G/A, G215A and Y217L/I/V/M, wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%.

In one embodiment of this aspect of the invention, the subtilase variant comprises the substitutions Y104V/I/L/M+G128S/A/T, preferably Y104V+G128S, and further comprises a substitution in position 9 selected from S9E and S9D, preferably S9E.

In another embodiment, the subtilase variant comprises the substitutions Y104V/I/L/M+G128S/A/T, preferably Y104V+G128S, and further comprises a substitution in position 76 selected from N76D and N76E, preferably N76E.

In another embodiment, the subtilase variant comprises the substitutions Y104V/I/L/M+G128S/A/T, preferably Y104V+G128S, and further comprises a substitution in position 107 selected from I107L, I107V and I107M, preferably I107L.

In another embodiment, the subtilase variant comprises the substitutions Y104V/I/L/M+G128S/A/T, preferably Y104V+G128S, and further comprises a substitution in position 131 selected from G131* and G131P.

In another embodiment, the subtilase variant comprises the substitutions Y104V/I/L/M+G128S/A/T, preferably Y104V+G128S, and further comprises a substitution in position 159 selected from S159E and S159D, preferably S159E.

In another embodiment, the subtilase variant comprises the substitutions Y104V/I/L/M+G128S/A/T, preferably Y104V+G128S, and further comprises a substitution in position 204 selected from S204D and S204E, preferably S204D.

In another embodiment, the subtilase variant comprises the substitutions Y104V/I/L/M+G128S/A/T, preferably Y104V+G128S, and further comprises a substitution in position 206 selected from Q206L, Q206I, Q206V and Q206M, preferably Q206L.

In another embodiment, the subtilase variant comprises the substitutions Y104V/I/L/M+G128S/A/T, preferably Y104V+G128S, and further comprises a substitution in position 212 selected from N212G, N212A and N212S, preferably N212G.

In another embodiment, the subtilase variant comprises the substitutions Y104V/I/L/M+G128S/A/T, preferably Y104V+G128S, and further comprises a substitution in position 216 selected from A216V, A216I, A216L and A216M, preferably A216V.

In another embodiment, the subtilase variant comprises the substitutions Y104V/I/L/M+G128S/A/T, preferably Y104V+G128S, and further comprises a substitution in position 76 selected from N76D and N76E, preferably N76D, and a mutation in position 131 selected from G131* and G131P. Exemplary variants of this embodiment comprise or consist of the substitutions N76D+Y104V+G128S+G131* or N76D+Y104V+G128S+G131P.

In another embodiment, the subtilase variant comprises the substitutions Y104V/I/L/M+G128S/A/T, preferably Y104V+G128S, and further comprises a substitution in position 76 selected from N76D and N76E, preferably N76D, a mutation in position 131 selected from G131* and G131P, and a substitution in position 212 selected from N212G, N212A and N212S, preferably N212G. Exemplary variants of this embodiment comprise or consist of the substitutions N76D+Y104V+G128S+G131*+N212G or N76D+Y104V+G128S+G131P+N212G.

In another embodiment, the subtilase variant comprises the substitutions Y104V/I/L/M+G128S/A/T, preferably Y104V+G128S, and further comprises a mutation in position 131 selected from G131* and G131P, and a substitution in position 204 selected from S204D and S204E, preferably S204D. Exemplary variants of this embodiment comprise or consist of the substitutions Y104V+G128S+G131*+Q204D or Y104V+G128S+G131P+Q204D.

In another embodiment, the subtilase variant comprises the substitutions Y104V/I/L/M+G128S/A/T, preferably Y104V+G128S, and further comprises a mutation in position 131 selected from G131* and G131P, and a substitution in position 206 selected from Q206L, Q206I, Q206V and Q206M, preferably Q206L. Exemplary variants of this embodiment comprise or consist of the substitutions Y104V+G128S+G131*+Q206L or Y104V+G128S+G131P+Q206L.

In another embodiment, the subtilase variant comprises the substitutions Y104V/I/L/M+G128S/A/T, preferably Y104V+G128S, and further comprises a mutation in position 131 selected from G131* and G131P, and a substitution in position 212 selected from N212G, N212A and N212S, preferably N212G. Exemplary variants of this embodiment comprise or consist of the substitutions Y104V+G128S+G131*+N212G or Y104V+G128S+G131P+N212G.

In another embodiment, the subtilase variant comprises the substitutions Y104V/I/L/M+G128S/A/T, preferably Y104V+G128S, and further comprises a mutation in position 131 selected from G131* and G131P, and a substitution in position 216 selected from A216V, A216I, A216L and A216M, preferably A216V. Exemplary variants of this embodiment comprise or consist of the substitutions Y104V+G128S+G131*+A216V or Y104V+G128S+G131P+A216V.

In another embodiment, the subtilase variant comprises the substitutions Y104V/I/L/M+G128S/A/T, preferably Y104V+G128S, and further comprises a mutation in position 131 selected from G131* and G131P, and a substitution in position 159 selected from S159E and S159D, preferably S159E. Exemplary variants of this embodiment comprise or consist of the substitutions Y104V+G128S+G131*+S159E or Y104V+G128S+G131P+S159E.

In another embodiment, the subtilase variant comprises the substitutions Y104V/I/L/M+G128S/A/T, preferably Y104V+G128S, and further comprises a substitution in position 9 selected from S9E and S9D, preferably S9E, and a mutation in position 131 selected from G131* and G131P. Exemplary variants of this embodiment comprise or consist of the substitutions Y104V+G128S+S9E+G131* or Y104V+G128S+S9E+G131P.

In a particular embodiment of this aspect of the invention, the subtilase variant comprises or consists of the set of mutations N76D Y104V G128S G131* N212G.

In another particular embodiment, the subtilase variant comprises or consists of the set of mutations N76D Y104V G128S G131P.

In another particular embodiment, the subtilase variant comprises or consists of the set of mutations N76D Y104V G128S G131*.

In another particular embodiment, the subtilase variant comprises or consists of the set of mutations Y104V I107L G128S G131* Q206L.

In another particular embodiment, the subtilase variant comprises or consists of the set of mutations N76D Y104V G128S G131P N212G.

In another particular embodiment, the subtilase variant comprises or consists of the set of mutations S63G Y104V G128S G131* L209W G215A Y217L.

In another particular embodiment, the subtilase variant comprises or consists of the set of mutations Y104V G128S G131* Q206L A216V.

In another particular embodiment, the subtilase variant comprises or consists of the set of mutations S63G Y104V G128S G131P L209W G215A Y217L.

In another particular embodiment, the subtilase variant comprises or consists of the set of mutations Y104V G128S G131* Q206L.

In another particular embodiment, the subtilase variant comprises or consists of the set of mutations Y104V G128S G131* S159E Q206L A216V.

In another particular embodiment, the subtilase variant comprises or consists of the set of mutations Y104V G128S G131* S204D N212G.

In another particular embodiment, the subtilase variant comprises or consists of the set of mutations Y104V G128S G131P S204D N212G.

In another particular embodiment, the subtilase variant comprises or consists of the set of mutations Y104V G128S G131P Q206L A216V.

In another particular embodiment, the subtilase variant comprises or consists of the set of mutations S9E Y104V G128S G131*.

In another particular embodiment, the subtilase variant comprises or consists of the set of mutations Y104V G128S G131P Q206L.

In another particular embodiment, the subtilase variant comprises or consists of the set of mutations Y104V G128S G131P S159E Q206L.

In another particular embodiment, the subtilase variant comprises or consists of the set of mutations S9E Y104V G128S G131P.

In another particular embodiment, the subtilase variant comprises or consists of the set of mutations Y104V G128S G131P S159E Q206L A216V.

In a third aspect of the invention, the subtilase variant comprises or consists of at least three mutations, for example at least four mutations, selected from the group consisting of S9E/D, N76D/E, A88V/I/L/M, S159E/D, S204D/E, Q206L/I/V/M, L209W, N212G/A/S, A216V/I/L/M, Y217L/I/V/M F261W/N/T and Y262E/D, wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%.

In a particular embodiment of this aspect of the invention, the subtilase variant comprises or consists of the substitutions Q206L/I/V/M, N212G/A/S and A216V/I/L/M, preferably Q206L, N212G and A216V. The variant of this embodiment may further include one or more additional substitutions, for example one or more substitutions selected from S9E/D, N76D/E, S159E/D and S204D/E, preferably S204D/E, more preferably S204D.

In another embodiment of this aspect of the invention, the subtilase variant comprises or consists of the substitutions N76D/E, S159E/D, Q206L/I/V/M, N212G/A/S and A216V/I/L/M, preferably N76D, S159E, Q206L, N212G and A216V.

In another embodiment, the subtilase variant comprises or consists of the substitutions S204D/E, Q206L/I/V/M, N212G/A/S and A216V/I/L/M, preferably S204D, Q206L, N212G and A216V.

In another embodiment, the subtilase variant comprises or consists of the substitutions S159E/D, Q206L/I/V/M, N212G/A/S and A216V/I/L/M, preferably S159E, Q206L, N212G and A216V.

In another embodiment, the subtilase variant comprises or consists of the substitutions S9E/D, S159E/D, Q206L/I/V/M and A216V/I/L/M, preferably S9E, S159E, Q206L and A216V.

In another embodiment, the subtilase variant comprises or consists of the substitutions N76D/E, N212G/A/S, F261W/N/T and Y262E/D, preferably N76D, N212G, F261W and Y262E.

In another embodiment, the subtilase variant comprises or consists of the substitutions S204D/E, Q206L/I/V/M and N212G/A/S, preferably S204D, Q206L and N212G.

In another embodiment, the subtilase variant comprises or consists of the substitutions S9E/D, S204D/E and N212G/A/S, preferably S9E, S204D and N212G.

In another embodiment, the subtilase variant comprises or consists of the substitutions N76D/E, A88V/I/L/M, S204D/E and N212G/A/S, preferably N76D, A88V, S204D and N212G.

In another embodiment, the subtilase variant comprises or consists of the substitutions Q206L/I/V/M, F261W/N/T and Y262E/D, preferably Q206L, F261W and Y262E.

In another embodiment, the subtilase variant comprises or consists of the substitutions Q206L/I/V/M, L209W/N/T, A216V/I/L/M and Y217L/I/V/M, preferably Q206L, L209W, A216V and Y217L.

A further aspect of the invention relates to subtilase variants comprising two mutations in positions selected from 9, 63, 76, 88, 104, 107, 128, 131, 159, 204, 206, 209, 212, 215, 216, 261 and 262, wherein positions are numbered according to SEQ ID NO: 1, and wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, or at least 98%, but less than 100%. In this aspect of the invention, the mutations are in particular selected from the following:

the mutation in position 9 is S9E or S9D, preferably S9E;
the mutation in position 63 is S63G or S63A, preferably S63G;
the mutation in position 76 is N76D or N76E, preferably N76D;
the mutation in position 88 is A88V, A88I, A88L or A88M, preferably A88V;
the mutation in position 104 is Y104V, Y104I, Y104L or Y104M, preferably Y104V;
the mutation in position 107 is I107L, I107V, I107M, preferably I107L;
the mutation in position 128 is G128S, G128A or G128T, preferably G128S;
the mutation in position 131 is G131* or G131P;
the mutation in position 159 is S159E or S159D, preferably S159E;
the mutation in position 204 is S204D or S204E, preferably S204D;
the mutation in position 206 is Q206L, Q206I, Q206V or Q206M, preferably Q206L;
the mutation in position 209 is L209W;
the mutation in position 212 is N212G, N212A or N212S, preferably N212G;
the mutation in position 215 is G215A;
the mutation in position 216 is A216V, A216I, A216L or A216M, preferably A216V;
the mutation in position 217 is Y217L, Y217I, Y217V or Y217M, preferably Y217L;
the mutation in position 261 is F261W, F261N or F261Y, preferably F261W; and/or
the mutation in position 262 is Y262E or Y262D, preferably Y262E.

In one embodiment of this aspect of the invention, the variant comprises a first mutation S9E or S9D, preferably S9E, and a second mutation S63G or S63A, preferably S63G.

In another embodiment, the variant comprises a first mutation S9E or S9D, preferably S9E, and a second mutation N76D or N76E, preferably N76D.

In another embodiment, the variant comprises a first mutation S9E or S9D, preferably S9E, and a second mutation A88V, A88I, A88L or A88M, preferably A88V.

In another embodiment, the variant comprises a first mutation S9E or S9D, preferably S9E, and a second mutation Y104V, Y104I, Y104L or Y104M, preferably Y104V.

In another embodiment, the variant comprises a first mutation S9E or S9D, preferably S9E, and a second mutation I107L, I107V, I107M, preferably I107L.

In another embodiment, the variant comprises a first mutation S9E or S9D, preferably S9E, and a second mutation G128S, G128A or G128T, preferably G128S.

In another embodiment, the variant comprises a first mutation S9E or S9D, preferably S9E, and a second mutation G131*.

In another embodiment, the variant comprises a first mutation S9E or S9D, preferably S9E, and a second mutation G131P.

In another embodiment, the variant comprises a first mutation S9E or S9D, preferably S9E, and a second mutation S159E or S159D, preferably S159E.

In another embodiment, the variant comprises a first mutation S9E or S9D, preferably S9E, and a second mutation S204D or S204E, preferably S204D.

In another embodiment, the variant comprises a first mutation S9E or S9D, preferably S9E, and a second mutation Q206L, Q206I, Q206V or Q206M, preferably Q206L.

In another embodiment, the variant comprises a first mutation S9E or S9D, preferably S9E, and a second mutation L209W.

In another embodiment, the variant comprises a first mutation S9E or S9D, preferably S9E, and a second mutation N212G, N212A or N212S, preferably N212G.

In another embodiment, the variant comprises a first mutation S9E or S9D, preferably S9E, and a second mutation G215A.

In another embodiment, the variant comprises a first mutation S9E or S9D, preferably S9E, and a second mutation A216V, A216I, A216L or A216M, preferably A216V.

In another embodiment, the variant comprises a first mutation S9E or S9D, preferably S9E, and a second mutation Y217L, Y217I, Y217V or Y217M, preferably Y217L.

In another embodiment, the variant comprises a first mutation S9E or S9D, preferably S9E, and a second mutation F261W, F261N or F261Y, preferably F261W.

In another embodiment, the variant comprises a first mutation S9E or S9D, preferably S9E, and a second mutation Y262E or Y262D, preferably Y262E.

In another embodiment, the variant comprises a first mutation S63G or S63A, preferably S63G, and a second mutation N76D or N76E, preferably N76D.

In another embodiment, the variant comprises a first mutation S63G or S63A, preferably S63G, and a second mutation A88V, A88I, A88L or A88M, preferably A88V.

In another embodiment, the variant comprises a first mutation S63G or S63A, preferably S63G, and a second mutation Y104V, Y104I, Y104L or Y104M, preferably Y104V.

In another embodiment, the variant comprises a first mutation S63G or S63A, preferably S63G, and a second mutation I107L, I107V, I107M, preferably I107L.

In another embodiment, the variant comprises a first mutation S63G or S63A, preferably S63G, and a second mutation G128S, G128A or G128T, preferably G128S.

In another embodiment, the variant comprises a first mutation S63G or S63A, preferably S63G, and a second mutation G131*.

In another embodiment, the variant comprises a first mutation S63G or S63A, preferably S63G, and a second mutation G131P.

In another embodiment, the variant comprises a first mutation S63G or S63A, preferably S63G, and a second mutation S159E or S159D, preferably S159E.

In another embodiment, the variant comprises a first mutation S63G or S63A, preferably S63G, and a second mutation S204D or S204E, preferably S204D.

In another embodiment, the variant comprises a first mutation S63G or S63A, preferably S63G, and a second mutation Q206L, Q206I, Q206V or Q206M, preferably Q206L.

In another embodiment, the variant comprises a first mutation S63G or S63A, preferably S63G, and a second mutation L209W.

In another embodiment, the variant comprises a first mutation S63G or S63A, preferably S63G, and a second mutation N212G, N212A or N212S, preferably N212G.

In another embodiment, the variant comprises a first mutation S63G or S63A, preferably S63G, and a second mutation G215A.

In another embodiment, the variant comprises a first mutation S63G or S63A, preferably S63G, and a second mutation A216V, A216I, A216L or A216M, preferably A216V.

In another embodiment, the variant comprises a first mutation S63G or S63A, preferably S63G, and a second mutation Y217L, Y217I, Y217V or Y217M, preferably Y217L.

In another embodiment, the variant comprises a first mutation S63G or S63A, preferably S63G, and a second mutation F261W, F261N or F261Y, preferably F261W.

In another embodiment, the variant comprises a first mutation S63G or S63A, preferably S63G, and a second mutation Y262E or Y262D, preferably Y262E.

In another embodiment, the variant comprises a first mutation N76D or N76E, preferably N76D, and a second mutation A88V, A88I, A88L or A88M, preferably A88V.

In another embodiment, the variant comprises a first mutation N76D or N76E, preferably N76D, and a second mutation Y104V, Y104I, Y104L or Y104M, preferably Y104V.

In another embodiment, the variant comprises a first mutation N76D or N76E, preferably N76D, and a second mutation I107L, I107V, I107M, preferably I107L.

In another embodiment, the variant comprises a first mutation N76D or N76E, preferably N76D, and a second mutation G128S, G128A or G128T, preferably G128S.

In another embodiment, the variant comprises a first mutation N76D or N76E, preferably N76D, and a second mutation G131*.

In another embodiment, the variant comprises a first mutation N76D or N76E, preferably N76D, and a second mutation G131P.

In another embodiment, the variant comprises a first mutation N76D or N76E, preferably N76D, and a second mutation S159E or S159D, preferably S159E.

In another embodiment, the variant comprises a first mutation N76D or N76E, preferably N76D, and a second mutation S204D or S204E, preferably S204D.

In another embodiment, the variant comprises a first mutation N76D or N76E, preferably N76D, and a second mutation Q206L, Q206I, Q206V or Q206M, preferably Q206L.

In another embodiment, the variant comprises a first mutation N76D or N76E, preferably N76D, and a second mutation L209W.

In another embodiment, the variant comprises a first mutation N76D or N76E, preferably N76D, and a second mutation N212G, N212A or N212S, preferably N212G.

In another embodiment, the variant comprises a first mutation N76D or N76E, preferably N76D, and a second mutation G215A.

In another embodiment, the variant comprises a first mutation N76D or N76E, preferably N76D, and a second mutation A216V, A216I, A216L or A216M, preferably A216V.

In another embodiment, the variant comprises a first mutation N76D or N76E, preferably N76D, and a second mutation Y217L, Y217I, Y217V or Y217M, preferably Y217L.

In another embodiment, the variant comprises a first mutation N76D or N76E, preferably N76D, and a second mutation F261W, F261N or F261Y, preferably F261W.

In another embodiment, the variant comprises a first mutation N76D or N76E, preferably N76D, and a second mutation Y262E or Y262D, preferably Y262E.

In another embodiment, the variant comprises a first mutation A88V, A88I, A88L or A88M, preferably A88V, and a second mutation Y104V, Y104I, Y104L or Y104M, preferably Y104V.

In another embodiment, the variant comprises a first mutation A88V, A88I, A88L or A88M, preferably A88V, and a second mutation I107L, I107V, I107M, preferably I107L.

In another embodiment, the variant comprises a first mutation A88V, A88I, A88L or A88M, preferably A88V, and a second mutation G128S, G128A or G128T, preferably G128S.

In another embodiment, the variant comprises a first mutation A88V, A88I, A88L or A88M, preferably A88V, and a second mutation G131*.

In another embodiment, the variant comprises a first mutation A88V, A88I, A88L or A88M, preferably A88V, and a second mutation G131P.

In another embodiment, the variant comprises a first mutation A88V, A88I, A88L or A88M, preferably A88V, and a second mutation S159E or S159D, preferably S159E.

In another embodiment, the variant comprises a first mutation A88V, A88I, A88L or A88M, preferably A88V, and a second mutation S204D or S204E, preferably S204D.

In another embodiment, the variant comprises a first mutation A88V, A88I, A88L or A88M, preferably A88V, and a second mutation Q206L, Q206I, Q206V or Q206M, preferably Q206L.

In another embodiment, the variant comprises a first mutation A88V, A88I, A88L or A88M, preferably A88V, and a second mutation L209W.

In another embodiment, the variant comprises a first mutation A88V, A88I, A88L or A88M, preferably A88V, and a second mutation N212G, N212A or N212S, preferably N212G.

In another embodiment, the variant comprises a first mutation A88V, A88I, A88L or A88M, preferably A88V, and a second mutation G215A.

In another embodiment, the variant comprises a first mutation A88V, A88I, A88L or A88M, preferably A88V, and a second mutation A216V, A216I, A216L or A216M, preferably A216V.

In another embodiment, the variant comprises a first mutation A88V, A88I, A88L or A88M, preferably A88V, and a second mutation Y217L, Y217I, Y217V or Y217M, preferably Y217L.

In another embodiment, the variant comprises a first mutation A88V, A88I, A88L or A88M, preferably A88V, and a second mutation F261W, F261N or F261Y, preferably F261W.

In another embodiment, the variant comprises a first mutation A88V, A88I, A88L or A88M, preferably A88V, and a second mutation Y262E or Y262D, preferably Y262E.

In another embodiment, the variant comprises a first mutation Y104V, Y104I, Y104L or Y104M, preferably Y104V, and a second mutation I107L, I107V, I107M, preferably I107L.

In another embodiment, the variant comprises a first mutation Y104V, Y104I, Y104L or Y104M, preferably Y104V, and a second mutation G128S, G128A or G128T, preferably G128S.

In another embodiment, the variant comprises a first mutation Y104V, Y104I, Y104L or Y104M, preferably Y104V, and a second mutation G131*.

In another embodiment, the variant comprises a first mutation Y104V, Y104I, Y104L or Y104M, preferably Y104V, and a second mutation G131P.

In another embodiment, the variant comprises a first mutation Y104V, Y104I, Y104L or Y104M, preferably Y104V, and a second mutation S159E or S159D, preferably S159E.

In another embodiment, the variant comprises a first mutation Y104V, Y104I, Y104L or Y104M, preferably Y104V, and a second mutation S204D or S204E, preferably S204D.

In another embodiment, the variant comprises a first mutation Y104V, Y104I, Y104L or Y104M, preferably Y104V, and a second mutation Q206L, Q206I, Q206V or Q206M, preferably Q206L.

In another embodiment, the variant comprises a first mutation Y104V, Y104I, Y104L or Y104M, preferably Y104V, and a second mutation L209W.

In another embodiment, the variant comprises a first mutation Y104V, Y104I, Y104L or Y104M, preferably Y104V, and a second mutation N212G, N212A or N212S, preferably N212G.

In another embodiment, the variant comprises a first mutation Y104V, Y104I, Y104L or Y104M, preferably Y104V, and a second mutation G215A.

In another embodiment, the variant comprises a first mutation Y104V, Y104I, Y104L or Y104M, preferably Y104V, and a second mutation A216V, A216I, A216L or A216M, preferably A216V.

In another embodiment, the variant comprises a first mutation Y104V, Y104I, Y104L or Y104M, preferably Y104V, and a second mutation Y217L, Y217I, Y217V or Y217M, preferably Y217L.

In another embodiment, the variant comprises a first mutation Y104V, Y104I, Y104L or Y104M, preferably Y104V, and a second mutation F261W, F261N or F261Y, preferably F261W.

In another embodiment, the variant comprises a first mutation Y104V, Y104I, Y104L or Y104M, preferably Y104V, and a second mutation Y262E or Y262D, preferably Y262E.

In another embodiment, the variant comprises a first mutation I107L, I107V, I107M, preferably I107L, and a second mutation G128S, G128A or G128T, preferably G128S.

In another embodiment, the variant comprises a first mutation I107L, I107V, I107M, preferably I107L, and a second mutation G131*.

In another embodiment, the variant comprises a first mutation I107L, I107V, I107M, preferably I107L, and a second mutation G131P.

In another embodiment, the variant comprises a first mutation I107L, I107V, I107M, preferably I107L, and a second mutation S159E or S159D, preferably S159E.

In another embodiment, the variant comprises a first mutation I107L, I107V, I107M, preferably I107L, and a second mutation S204D or S204E, preferably S204D.

In another embodiment, the variant comprises a first mutation I107L, I107V, I107M, preferably I107L, and a second mutation Q206L, Q206I, Q206V or Q206M, preferably Q206L.

In another embodiment, the variant comprises a first mutation I107L, I107V, I107M, preferably I107L, and a second mutation L209W.

In another embodiment, the variant comprises a first mutation I107L, I107V, I107M, preferably I107L, and a second mutation N212G, N212A or N212S, preferably N212G.

In another embodiment, the variant comprises a first mutation I107L, I107V, I107M, preferably I107L, and a second mutation G215A.

In another embodiment, the variant comprises a first mutation I107L, I107V, I107M, preferably I107L, and a second mutation A216V, A216I, A216L or A216M, preferably A216V.

In another embodiment, the variant comprises a first mutation I107L, I107V, I107M, preferably I107L, and a second mutation Y217L, Y217I, Y217V or Y217M, preferably Y217L.

In another embodiment, the variant comprises a first mutation I107L, I107V, I107M, preferably I107L, and a second mutation F261W, F261N or F261Y, preferably F261W.

In another embodiment, the variant comprises a first mutation I107L, I107V, I107M, preferably I107L, and a second mutation Y262E or Y262D, preferably Y262E.

In another embodiment, the variant comprises a first mutation G128S, G128A or G128T, preferably G128S, and a second mutation G131*.

In another embodiment, the variant comprises a first mutation G128S, G128A or G128T, preferably G128S, and a second mutation G131P.

In another embodiment, the variant comprises a first mutation G128S, G128A or G128T, preferably G128S, and a second mutation S159E or S159D, preferably S159E.

In another embodiment, the variant comprises a first mutation G128S, G128A or G128T, preferably G128S, and a second mutation S204D or S204E, preferably S204D.

In another embodiment, the variant comprises a first mutation G128S, G128A or G128T, preferably G128S, and a second mutation Q206L, Q206I, Q206V or Q206M, preferably Q206L.

In another embodiment, the variant comprises a first mutation G128S, G128A or G128T, preferably G128S, and a second mutation L209W.

In another embodiment, the variant comprises a first mutation G128S, G128A or G128T, preferably G128S, and a second mutation N212G, N212A or N212S, preferably N212G.

In another embodiment, the variant comprises a first mutation G128S, G128A or G128T, preferably G128S, and a second mutation G215A.

In another embodiment, the variant comprises a first mutation G128S, G128A or G128T, preferably G128S, and a second mutation A216V, A216I, A216L or A216M, preferably A216V.

In another embodiment, the variant comprises a first mutation G128S, G128A or G128T, preferably G128S, and a second mutation Y217L, Y217I, Y217V or Y217M, preferably Y217L.

In another embodiment, the variant comprises a first mutation G128S, G128A or G128T, preferably G128S, and a second mutation F261W, F261N or F261Y, preferably F261W.

In another embodiment, the variant comprises a first mutation G128S, G128A or G128T, preferably G128S, and a second mutation Y262E or Y262D, preferably Y262E.

In another embodiment, the variant comprises a first mutation G131*, and a second mutation S159E or S159D, preferably S159E.

In another embodiment, the variant comprises a first mutation G131*, and a second mutation S204D or S204E, preferably S204D.

In another embodiment, the variant comprises a first mutation G131*, and a second mutation Q206L, Q206I, Q206V or Q206M, preferably Q206L.

In another embodiment, the variant comprises a first mutation G131*, and a second mutation L209W.

In another embodiment, the variant comprises a first mutation G131*, and a second mutation N212G, N212A or N212S, preferably N212G.

In another embodiment, the variant comprises a first mutation G131*, and a second mutation G215A.

In another embodiment, the variant comprises a first mutation G131*, and a second mutation A216V, A216I, A216L or A216M, preferably A216V.

In another embodiment, the variant comprises a first mutation G131*, and a second mutation Y217L, Y217I, Y217V or Y217M, preferably Y217L.

In another embodiment, the variant comprises a first mutation G131*, and a second mutation F261W, F261N or F261Y, preferably F261W.

In another embodiment, the variant comprises a first mutation G131*, and a second mutation Y262E or Y262D, preferably Y262E.

In another embodiment, the variant comprises a first mutation G131P, and a second mutation S159E or S159D, preferably S159E.

In another embodiment, the variant comprises a first mutation G131P, and a second mutation S204D or S204E, preferably S204D.

In another embodiment, the variant comprises a first mutation G131P, and a second mutation Q206L, Q206I, Q206V or Q206M, preferably Q206L.

In another embodiment, the variant comprises a first mutation G131P, and a second mutation L209W.

In another embodiment, the variant comprises a first mutation G131P, and a second mutation N212G, N212A or N212S, preferably N212G.

In another embodiment, the variant comprises a first mutation G131P, and a second mutation G215A.

In another embodiment, the variant comprises a first mutation G131P, and a second mutation A216V, A216I, A216L or A216M, preferably A216V.

In another embodiment, the variant comprises a first mutation G131P, and a second mutation Y217L, Y217I, Y217V or Y217M, preferably Y217L.

In another embodiment, the variant comprises a first mutation G131P, and a second mutation F261W, F261N or F261Y, preferably F261W.

In another embodiment, the variant comprises a first mutation G131P, and a second mutation Y262E or Y262D, preferably Y262E.

In another embodiment, the variant comprises a first mutation S159E or S159D, preferably S159E, and a second mutation S204D or S204E, preferably S204D.

In another embodiment, the variant comprises a first mutation S159E or S159D, preferably S159E, and a second mutation Q206L, Q206I, Q206V or Q206M, preferably Q206L.

In another embodiment, the variant comprises a first mutation S159E or S159D, preferably S159E, and a second mutation L209W.

In another embodiment, the variant comprises a first mutation S159E or S159D, preferably S159E, and a second mutation N212G, N212A or N212S, preferably N212G.

In another embodiment, the variant comprises a first mutation S159E or S159D, preferably S159E, and a second mutation G215A.

In another embodiment, the variant comprises a first mutation S159E or S159D, preferably S159E, and a second mutation A216V, A216I, A216L or A216M, preferably A216V.

In another embodiment, the variant comprises a first mutation S159E or S159D, preferably S159E, and a second mutation Y217L, Y217I, Y217V or Y217M, preferably Y217L.

In another embodiment, the variant comprises a first mutation S159E or S159D, preferably S159E, and a second mutation F261W, F261N or F261Y, preferably F261W.

In another embodiment, the variant comprises a first mutation S159E or S159D, preferably S159E, and a second mutation Y262E or Y262D, preferably Y262E.

In another embodiment, the variant comprises a first mutation S204D or S204E, preferably S204D, and a second mutation Q206L, Q206I, Q206V or Q206M, preferably Q206L.

In another embodiment, the variant comprises a first mutation S204D or S204E, preferably S204D, and a second mutation L209W.

In another embodiment, the variant comprises a first mutation S204D or S204E, preferably S204D, and a second mutation N212G, N212A or N212S, preferably N212G.

In another embodiment, the variant comprises a first mutation S204D or S204E, preferably S204D, and a second mutation G215A.

In another embodiment, the variant comprises a first mutation S204D or S204E, preferably S204D, and a second mutation A216V, A216I, A216L or A216M, preferably A216V.

In another embodiment, the variant comprises a first mutation S204D or S204E, preferably S204D, and a second mutation Y217L, Y217I, Y217V or Y217M, preferably Y217L.

In another embodiment, the variant comprises a first mutation S204D or S204E, preferably S204D, and a second mutation F261W, F261N or F261Y, preferably F261W.

In another embodiment, the variant comprises a first mutation S204D or S204E, preferably S204D, and a second mutation Y262E or Y262D, preferably Y262E.

In another embodiment, the variant comprises a first mutation Q206L, Q206I, Q206V or Q206M, preferably Q206L, and a second mutation L209W.

In another embodiment, the variant comprises a first mutation Q206L, Q206I, Q206V or Q206M, preferably Q206L, and a second mutation N212G, N212A or N212S, preferably N212G.

In another embodiment, the variant comprises a first mutation Q206L, Q206I, Q206V or Q206M, preferably Q206L, and a second mutation G215A.

In another embodiment, the variant comprises a first mutation Q206L, Q206I, Q206V or Q206M, preferably Q206L, and a second mutation A216V, A216I, A216L or A216M, preferably A216V.

In another embodiment, the variant comprises a first mutation Q206L, Q206I, Q206V or Q206M, preferably Q206L, and a second mutation Y217L, Y217I, Y217V or Y217M, preferably Y217L.

In another embodiment, the variant comprises a first mutation Q206L, Q206I, Q206V or Q206M, preferably Q206L, and a second mutation F261W, F261N or F261Y, preferably F261W.

In another embodiment, the variant comprises a first mutation Q206L, Q206I, Q206V or Q206M, preferably Q206L, and a second mutation Y262E or Y262D, preferably Y262E.

In another embodiment, the variant comprises a first mutation L209W, and a second mutation N212G, N212A or N212S, preferably N212G.

In another embodiment, the variant comprises a first mutation L209W, and a second mutation G215A.

In another embodiment, the variant comprises a first mutation L209W, and a second mutation A216V, A216I, A216L or A216M, preferably A216V.

In another embodiment, the variant comprises a first mutation L209W, and a second mutation Y217L, Y217I, Y217V or Y217M, preferably Y217L.

In another embodiment, the variant comprises a first mutation L209W, and a second mutation F261W, F261N or F261Y, preferably F261W.

In another embodiment, the variant comprises a first mutation L209W, and a second mutation Y262E or Y262D, preferably Y262E.

In another embodiment, the variant comprises a first mutation N212G, N212A or N212S, preferably N212G, and a second mutation G215A.

In another embodiment, the variant comprises a first mutation N212G, N212A or N212S, preferably N212G, and a second mutation A216V, A216I, A216L or A216M, preferably A216V.

In another embodiment, the variant comprises a first mutation N212G, N212A or N212S, preferably N212G, and a second mutation Y217L, Y217I, Y217V or Y217M, preferably Y217L.

In another embodiment, the variant comprises a first mutation N212G, N212A or N212S, preferably N212G, and a second mutation F261W, F261N or F261Y, preferably F261W.

In another embodiment, the variant comprises a first mutation N212G, N212A or N212S, preferably N212G, and a second mutation Y262E or Y262D, preferably Y262E.

In another embodiment, the variant comprises a first mutation G215A, and a second mutation A216V, A216I, A216L or A216M, preferably A216V.

In another embodiment, the variant comprises a first mutation G215A, and a second mutation Y217L, Y217I, Y217V or Y217M, preferably Y217L.

In another embodiment, the variant comprises a first mutation G215A, and a second mutation F261W, F261N or F261Y, preferably F261W.

In another embodiment, the variant comprises a first mutation G215A, and a second mutation Y262E or Y262D, preferably Y262E.

In another embodiment, the variant comprises a first mutation A216V, A216I, A216L or A216M, preferably A216V, and a second mutation Y217L, Y217I, Y217V or Y217M, preferably Y217L.

In another embodiment, the variant comprises a first mutation A216V, A216I, A216L or A216M, preferably A216V, and a second mutation F261W, F261N or F261Y, preferably F261W.

In another embodiment, the variant comprises a first mutation A216V, A216I, A216L or A216M, preferably A216V, and a second mutation Y262E or Y262D, preferably Y262E.

In another embodiment, the variant comprises a first mutation Y217L, Y217I, Y217V or Y217M, preferably Y217L, and a second mutation F261W, F261N or F261Y, preferably F261W.

In another embodiment, the variant comprises a first mutation Y217L, Y217I, Y217V or Y217M, preferably Y217L, and a second mutation Y262E or Y262D, preferably Y262E.

In another embodiment, the variant comprises a first mutation F261W, F261N or F261Y, preferably F261W, and a second mutation Y262E or Y262D, preferably Y262E.

Any of the variants of the invention may have a sequence identity to the amino acid sequence of SEQ ID NO: 1 of at least 85%, for example at least 90%, at least 91%, at least 92%, at least 93%, at least 94%, at least 95%, at least 96%, at least 97%, or at least 98%, but less than 100%.

The number of alterations in the variants of the present invention compared to SEQ ID NO: 1 may, for example, be in the range of 1-20, e.g., 1-10 or 1-5, such as 1, 2, 3, 4, 5, 6, 7, 8, 9 or 10 alterations.

In addition to the amino acid alterations specifically disclosed herein, a protease variant of the invention may comprise additional alterations at one or more other positions. These additional alterations may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, in *The Proteins*, Academic Press, New York. Common conservative substitution groups include, but are not limited to: G=A=S; I=V=L=M; D=E; Y=F; and N=Q (where e.g. "G=A=S" means that these three amino acids may be substituted for each other).

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. For BPN' (SEQ ID NO: 1) the catalytic triad comprising the amino acids S221, H64, and D32 is considered essential for protease activity of the enzyme.

The polypeptides of the invention may consist of 220 to 330 amino acids, such as 240 to 300, 260 to 290 or 270 to 280 amino acids.

Method for Stabilizing a Subtilase Variant

Another aspect of the invention relates to a method for stabilizing a subtilase variant, the method comprising introducing into a parent subtilase having protease activity and at least 80% sequence identity to SEQ ID NO: 1, for example at least 85%, at least 90%, at least 91%, at least 92%, at least 93%, at least 94%, at least 95%, at least 96%, at least 97%, at least 98%, at least 99% or 100% sequence identity, at least three mutations selected from:

(i) L209W in combination with two or more substitutions selected from S63G/A, G215A and Y217L/I/V/M;

(ii) Y104V/I/L/M and G128S/A/T in combination with at least one mutation, e.g. two, three or more mutations, selected from S9E/D, S63G/A, N76D/E, I107L/V/M, G131*, G131P, S159E/D, S204D/E, Q206L/I/N/M, N212G/A/S, G215A, A216V/I/L/M and Y217L/I/N/M;

(iii) S9E/D in combination with at least two substitutions selected from N76D/E, S204D/E and N212G/A/S;

(iv) N76D/E in combination with at least two substitutions selected from S9E/D, A88V/I/L/M, S159E/D, S204D/E, Q206L/I/V/M, N212G/A/S, A216V/I/L/M, F261W/N/Y and Y262E/D;

(v) Q206L/I/V/M in combination with at least two substitutions selected from S9E/D, N76D/E, S159E/D, S204D/E, L209W/N/Y, N212G/A/S, A216V/I/L/M, Y217L/I/V/M, F261W/N/Y and Y262E/D; and (vi) S204D/E, N212G/A/S and A216V/I/L/M, preferably in combination with at least one substitution selected from S9E/D, S159E/D and Q206L/I/V/M.

In the case of (i) in the method for stabilizing a subtilase variant above, the mutations may e.g. comprise S63G, L209W, G215A and Y217L; and optionally one or more additional mutations such one, two, three or more mutations selected from S9E/D, N76D/E, Y104V/I/L/M, G128S/A/T, G131*, G131P, S204D/E, Q206L/I/V/M, A216V/I/L/M, F261W/N/Y and Y262E/D; e.g. one, two, three or more mutations selected from S9E, N76D, Y104V, G128S, G131* or G131P, S204D, Q206L, A216V, F261W and Y262E.

In the case of (ii) in the method for stabilizing a subtilase variant above, the mutations may e.g. comprise Y104V and G128S in combination with at least one mutation, e.g. two, three or more mutations, selected from S9E, S63G, N76D, I107L, G131* or G131P, S159E, S204D, Q206L, N212G, G215A, A216V and Y217L.

In the case of (iii) in the method for stabilizing a subtilase variant above, the mutations may e.g. comprise S9E in combination with at least two substitutions selected from N76D, S204D and N212G.

In the case of (iv) in the method for stabilizing a subtilase variant above, the mutations may e.g. comprise N76D in combination with at least two substitutions selected from S9E, A88V, S159E, S204D, Q206L, N212G, A216V, F261W and Y262E.

In the case of (v) in the method for stabilizing a subtilase variant above, the mutations may e.g. comprise Q206L in combination with at least two substitutions selected from S9E, N76D, S159E, S204D, L209W, N212G, A216V, Y217L, F261W and Y262E.

In the case of (vi) in the method for stabilizing a subtilase variant above, the mutations may e.g. comprise S204D, Q206L, N212G and A216V.

It will be understood that the method for stabilizing a subtilase variant is meant to encompass introducing into the parent subtilase any combination of mutations disclosed above under the heading "Variants".

The variants of the invention, or the variants stabilized by the method above, preferably have an increased storage stability in a detergent composition compared to the subtilase of SEQ ID NO: 1.

Storage Stability

In one aspect, any of the protease variants of the invention, or protease variants stabilized by the method above, have an increased storage stability in a detergent composition compared to the subtilase of SEQ ID NO: 1. Storage stability may suitably be measured as described in storage stability assay I in Example 2 herein, and/or as measured as described in storage stability assay II in Example 3 herein.

Preferably, the protease variants of the invention, or protease variants stabilized by the method above, have an increased storage stability in a detergent composition compared to the subtilase of SEQ ID NO: 1 of at least 25%, preferably at least 50%, more preferably at least 75%, such as at least 100%, when measured for 24 hours as described in storage stability assay I in Example 2 herein, and/or as measured as described in storage stability assay II in Example 3 herein.

Parent Subtilases

The parent subtilase of a variant of the invention will typically be a protease that has at least 75% identity with the sequence of subtilisin BPN' from *Bacillus amyloliquefaciens*, which has the sequence of SEQ ID NO: 1. In preferred embodiments, the parent subtilase may have at least 80% identity to SEQ ID NO: 1, such as at least 85%, at least 90%, at least 91%, at least 92%, at least 93%, at least 94%, at least 95%, at least 96%, at least 97%, at least 98% or at least 99% identity with SEQ ID NO: 1. Alternatively, the parent subtilase may have a sequence that comprises of consists of SEQ ID NO: 1.

The parent may thus, for example, have the sequence of a wild-type subtilase such as BPN' (SEQ ID NO: 1), or alternatively may be a variant of BPN'. The parent may also be a related subtilase, e.g. from the S8A family having at least 75% sequence identity to SEQ ID NO: 1 as indicated above.

In one embodiment, the amino acid sequence of the parent may for example differ by up to 20 amino acids, such as up to 10 amino acids, e.g., 1, 2, 3, 4, 5, 6, 7, 8, 9, or 10 amino acids, from the polypeptide of SEQ ID NO: 1.

The parent subtilase may also be a fragment of the polypeptide of SEQ ID NO: 1 that has protease activity, or an allelic variant of the polypeptide of SEQ ID NO: 1.

The parent subtilase may be obtained from a microorganism of any suitable genus, in particular from a suitable bacteria genus. The parent subtilase is thus typically a bacterial subtilase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus* or *Streptomyces* subtilase, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* subtilase.

In one embodiment, the parent is obtained from a species of *Bacillus*. The parent may thus e.g. be a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis* or *Bacillus thuringiensis* subtilase.

In one embodiment, the parent is a *Bacillus amyloliquefaciens* protease, e.g. the protease of SEQ ID NO: 1.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, compost, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method for obtaining a subtilase variant, the method comprising (a) providing a host cell comprising a polynucleotide encoding a variant of a parent protease having three or more mutations, e.g. four or more mutations, compared to SEQ ID NO: 1, wherein the variant has protease activity and a sequence identity to SEQ ID NO: 1 of at least 80%, for example at least 85%, at least 90%, at least 91%, at least 92%, at least 93%, at least 94%, at least 95%, at least 96%, at least 97%, at least 98%, at least 99% or 100% sequence identity, and wherein the mutations are selected from:
(i) L209W in combination with two or more substitutions selected from S63G/A, G215A and Y217L/I/V/M;
(ii) Y104V/I/L/M and G128S/A/T in combination with at least one mutation selected from S9E/D, S63G/A, N76D/E, I107L/V/M, G131*, G131P, S159E/D, S204D/E, Q206L/I/V/M, N212G/A/S, G215A, A216V/I/L/M and Y217L/I/V/M;
(iii) S9E/D in combination with at least two substitutions selected from N76D/E, S204D/E and N212G/A/S;
(iv) N76D/E in combination with at least two substitutions selected from S9E/D, A88V/I/L/M, S159E/D, S204D/E, Q206L/I/V/M, N212G/A/S, A216V/I/L/M, F261W/N/Y and Y262E/D;
(v) Q206L/I/V/M in combination with at least two substitutions selected from S9E/D, N76D/E, S159E/D, S204D/E, L209W/N/Y, N212G/A/S, A216V/I/L/M, Y217L/I/V/M, F261W/N/Y and Y262E/D; and
(vi) S204D/E, N212G/A/S and A216V/I/L/M, preferably in combination with at least one substitution selected from S9E/D, S159E/D and Q206L/I/V/M;
(b) cultivating the host cell under conditions suitable for expression of the variant; and
(c) recovering the variant.

The variants can be prepared using any mutagenesis procedure known in the art, such as site-directed mutagenesis, synthetic gene construction, semi-synthetic gene construction, random mutagenesis, DNA shuffling, etc. For information on use of these mutagenesis techniques, see e.g. WO 2017/207762.

In the case of (i) in the method for obtaining a subtilase variant above, the mutations may e.g. comprise S63G, L209W, G215A and Y217L; and optionally one or more additional mutations such one, two, three or more mutations selected from S9E/D, N76D/E, Y104V/I/L/M, G128S/A/T, G131*, G131P, S204D/E, Q206L/I/V/M, A216V/I/L/M, F261W/N/Y and Y262E/D; e.g. one, two, three or more mutations selected from S9E, N76D, Y104V, G128S, G131* or G131P, S204D, Q206L, A216V, F261W and Y262E.

In the case of (ii) in the method for obtaining a subtilase variant above, the mutations may e.g. comprise Y104V and G128S in combination with at least one mutation, e.g. two, three or more mutations, selected from S9E, S63G, N76D, I107L, G131* or G131P, S159E, S204D, Q206L, N212G, G215A, A216V and Y217L.

In the case of (iii) in the method for obtaining a subtilase variant above, the mutations may e.g. comprise S9E in combination with at least two substitutions selected from N76D, S204D and N212G.

In the case of (iv) in the method for obtaining a subtilase variant above, the mutations may e.g. comprise N76D in combination with at least two substitutions selected from S9E, A88V, S159E, S204D, Q206L, N212G, A216V, F261W and Y262E.

In the case of (v) in the method for obtaining a subtilase variant above, the mutations may e.g. comprise Q206L in combination with at least two substitutions selected from S9E, N76D, S159E, S204D, L209W, N212G, A216V, Y217L, F261W and Y262E.

In the case of (vi) in the method for obtaining a subtilase variant above, the mutations may e.g. comprise S204D, Q206L, N212G and A216V.

It will be understood that the method for obtaining a subtilase variant is meant to encompass expression and recovery of variants having any combination of mutations disclosed above under the heading "Variants".

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for and optimize expression of a variant. Techniques for modifying polynucleotides utilizing recombinant DNA methods are well known in the art. These include, e.g., the use of control sequences such as promoters, transcription terminators, mRNA stabilizer regions downstream of a promoter and upstream of the coding sequence, signal peptide coding regions, propeptide coding sequences and regulatory sequences. For further information, see e.g. WO 2017/207762.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

For information on expression vectors, see e.g. WO 2017/207762.

Host Cells

The present invention also relates to recombinant host cells comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier.

The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell will typically be a Gram-positive or Gram-negative bacterium, such as a Gram-positive bacterium selected from *Bacillus, Clostridium, Enterococcus, Geobacillus, Lactobacillus, Lactococcus, Oceanobacillus, Staphylococcus, Streptococcus* and *Streptomyces*, or a Gram-negative bacterium selected from *Campylobacter, E. coli, Flavobacterium, Fusobacterium, Helicobacter, Ilyobacter, Neisseria, Pseudomonas, Salmonella* and *Ureaplasma*.

The bacterial host cell may e.g. be a *Bacillus* cell selected from *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis* and *Bacillus thuringiensis* cells.

For information on suitable host cells, see e.g. WO 2017/207762.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid-state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity, and may be recovered and purified using methods known in the art. See e.g. WO 2017/207762 for further information.

Compositions

The invention also relates to a composition comprising a subtilase variant of the invention, e.g. a detergent or cleaning composition.

The invention also relates to a composition comprising a subtilase variant of the invention and further comprising: one or more detergent components; and/or one or more additional enzymes. In a preferred embodiment, the composition is a detergent composition comprising one or more detergent components.

The present invention also relates to a composition comprising a subtilase variant of the present invention and further comprising one or more additional enzymes selected from the group consisting of amylases, catalases, cellulases (e.g., endoglucanases), cutinases, haloperoxygenases, lipases, mannanases, pectinases, pectin lyases, peroxidases, proteases, xanthanases, lichenases and xyloglucanases, or any mixture thereof.

A detergent composition may e.g. be in the form of a bar, a homogeneous tablet, a tablet having two or more layers, a pouch having one or more compartments, a regular or compact powder, a granule, a paste, a gel, or a regular, compact or concentrated liquid.

The invention also relates to use of a composition of the present in a cleaning process, such as laundry or hard surface cleaning such as dish wash.

The choice of additional components for a detergent composition is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product.

In a particular embodiment, a detergent composition comprises a subtilase variant of the invention and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

In one embodiment, one or more of the detergent components may be non-naturally occurring detergent components. In another embodiment, all of the detergent components may be non-naturally occurring detergent components.

In one embodiment, the subtilase variant of the invention may be added to a detergent composition in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

An automatic dish wash (ADW) composition may for example include 0.001%-30%, such as 0.01%-20%, such as 0.1-15%, such as 0.5-10% of enzyme protein by weight of the composition.

A granulated composition for laundry may for example include 0.001%-20%, such as 0.01%-10%, such as 0.05%-5% of enzyme protein by weight of the composition.

A liquid composition for laundry may for example include 0.0001%-10%, such as 0.001-7%, such as 0.1%-5% of enzyme protein by weight of the composition.

The enzymes such as the subtilase variant of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708 or the variants according to the invention may be stabilized using peptide aldehydes or ketones such as described in WO 2005/105826 and WO 2009/118375.

The subtilase variants of the invention may be formulated in liquid laundry compositions such as a liquid laundry compositions composition comprising:
 a) at least 0.01 mg of active subtilase variant per litre detergent,
 b) 2 wt % to 60 wt % of at least one surfactant
 c) 5 wt % to 50 wt % of at least one builder The detergent composition may be formulated into a granular detergent for laundry. Such detergent may comprise;
 a) at least 0.01 mg of active protease variant per gram of composition
 b) anionic surfactant, preferably 5 wt % to 50 wt %
 c) nonionic surfactant, preferably 1 wt % to 8 wt %
 d) builder, preferably 5 wt % to 40 wt %, such as carbonates, zeolites, phosphate builder, calcium sequestering builders or complexing agents.

Although components mentioned below are categorized by general header according to a particular functionality, this is not to be construed as a limitation, as a component may comprise additional functionalities as will be appreciated by the person skilled in the art.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized. Surfactants lower the surface tension in the detergent, which allows the stain being cleaned to be lifted and dispersed and then washed away.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alphaolefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein, the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein, the detergent will usually contain from about 0% to about 10% by weight of a zwitterionic surfactant. Non-limiting examples of zwitterionic surfactants include betaine, alkyldimethylbetaine, sulfobetaine, and combinations thereof.

Builders and Co-Builders

The detergent composition may contain about 0-65% by weight, such as about 5% to about 45% of a detergent builder or co-builder, or a mixture thereof. In a dish wash deteregent, the level of builder is typically 40-65%, particularly 50-65%. Builders and chelators soften, e.g., the wash water by removing the metal ions form the liquid. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis (methylenephosphonic acid) (DTPMPA or DTMPA), N-(2-hydroxyethyl) iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)-ethylidenediamine-N,N, N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 2009/102854 and U.S. Pat. No. 5,977,053.

The subtilase variants of the invention may also be formulated into a dish wash composition, preferably an automatic dish wash composition (ADW), comprising:
  a) at least 0.01 mg of active protease variant according to the invention, and
  b) 10-50 wt % builder preferably selected from citric acid, methylglycine-N,N-diacetic acid (MGDA) and/or glutamic acid-N,N-diacetic acid (GLDA) and mixtures thereof, and
  c) at least one bleach component.

Bleaching Systems

The detergent may contain 0-50% by weight, such as about 0.1% to about 25%, of a bleaching system. Bleach systems remove discolor often by oxidation, and many bleaches also have strong bactericidal properties, and are used for disinfecting and sterilizing. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like triacetin has the advantage that it is environmentally friendly as it eventually degrades into citric acid and alcohol. Furthermore, acetyl triethyl citrate and triacetin have good hydrolytic stability in the product upon storage and are efficient bleach activators. Finally, ATC provides a good building capacity to the laundry additive. Alternatively, the bleaching system may comprise peroxyacids of, for example, the amide, imide, or sulfone type. The bleaching system may also comprise peracids such as 6-(phthalimido) peroxyhexanoic acid (PAP). The bleaching system may also include a bleach catalyst or a booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2''-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, the bleach component may be an organic catalyst selected from the group consisting of organic catalysts having the following formula:

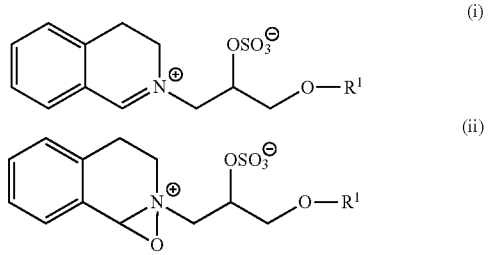

(i)

(ii)

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

Hydrotropes

A hydrotrope is a compound that solubilizes hydrophobic compounds in aqueous solutions (or oppositely, polar substances in a non-polar environment). Typically, hydrotropes have both hydrophilic and hydrophobic characters (so-called amphiphilic properties as known from surfactants); however, the molecular structures of hydrotropes generally do not favour spontaneous self-aggregation, see, e.g., review by Hodgdon and Kaler, 2007, Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behaviour, stability, and colloidal properties of systems containing substances of polar and non-polar character, including mixtures of water, oil, surfactants, and polymers. Hydrotropes are classically used across industries from pharma, personal care and food to technical applications. Use of hydrotropes in detergent compositions allows for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when the fabric is contacted with a wash liquor comprising the detergent compositions and thus altering the tint of the fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt % to 0.2 wt. % fabric hueing agent, this may be especially preferred when the composition is in the form of a unit dose pouch. Suitable hueing agents are also disclosed in, e.g., WO 2007/087257 and WO 2007/087243.

Additional Enzymes

The detergent additive as well as the detergent composition may comprise one or more (additional) enzymes such as an amylase, arabinase, carbohydrase, cellulase (e.g., endoglucanase), cutinase, galactanase, haloperoxygenase, lipase, mannanase, oxidase, e.g., laccase and/or peroxidase, pectinase, pectin lyase, protease, xylanase, xanthanase or xyloglucanase.

The properties of the selected enzyme(s) should be compatible with the selected detergent (e.g. pH-optimum, compatibility with other enzymatic and non-enzymatic ingredients, etc.).

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 495257, EP 531372, WO 96/11262, WO 96/29397, WO 98/08940. Other examples are cellulase variants such as those described in WO 94/07998, EP 531315, U.S. Pat. Nos. 5,457,046, 5,686,593, 5,763,254, WO 95/24471, WO 98/12307 and PCT/DK98/00299.

Examples of cellulases exhibiting endo-beta-1,4-glucanase activity (EC 3.2.1.4) are described in WO 02/99091.

Other examples of cellulases include the family 45 cellulases described in WO 96/29397, and especially variants thereof having substitution, insertion and/or deletion at one or more of the positions corresponding to the following positions in SEQ ID NO: 8 of WO 02/99091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases

The composition may comprise one or more additional proteases including those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloprotease may for example be a thermolysin from, e.g., family M4 or other metalloprotease such as those from M5, M7 or M8 families.

Examples of metalloproteases are the neutral metalloproteases as described in WO 2007/044993 (Genencor Int.) such as those derived from *Bacillus amyloliquefaciens*.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Purafect MAO, Purafect Ox®, Purafect OxP®, Puramax®, Properase®, FN2®, FN3®, FN4®, Excellase®, Eraser®, Opticlean® and Optimase® (Danisco/DuPont), Axapem™ (Gist-Brocades N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from Thermomyces, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe* grisea (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Amylases

Suitable amylases which can be used together with the subtilase variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Other suitable amylases are amylases having the sequence of SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N1280+T131I+T165I+K178L+T182G+Y305R+G475K,
wherein the variants are C-terminally truncated and optionally further comprise a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or a deletion in position R178 and/or S179 or of T180 and/or G181. Most preferred amylase variants of SEQ ID NO: 1 comprise the substitutions:

E187P+I203Y+G476K

E187P+I203Y+R458N+T459S+D460T+G476K and optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478.

More preferred variants of SEQ ID NO: 1 are those having the substitution in one of more of the following positions: N21D, D97N, V128I K177L, M200L, L204YF, E242QA, G477K and G478K and/or a deletion in position R179 and/or S180 or of I181 and/or G182. Most preferred amylase variants of SEQ ID NO: 1 comprise the substitutions N21D+D97N+V128I, and optionally further comprise a substitution at position 200 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particularly preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants: The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents: The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent: The detergent compositions of the present invention will preferably also contain additional components that may tint articles being cleaned, such as fluorescent whitening agent or optical brighteners. Where present the brightener is preferably at a level of about 0.01% to about 05%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1, 3-triazol-2-yl)stilbene-2,2'-disulphonate; 4,4'-bis-(2-anilino-4(1-methyl-2-hydroxy-ethylamino)-s- triazin-6-ylamino) stilbene-2,2'-disulphonate and 2-(stilbyl-4"-naptho-1.,2':4, 5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil release polymers: The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 03/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents: The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent enzyme(s), i.e. a subtilase variant of the invention and optionally one or more additional enzymes, may be included in a detergent composition by adding separate additives containing one or more enzymes, or by adding a combined additive comprising all of these enzymes. A detergent additive comprising one or more enzymes can be formulated, for example, as a granulate, liquid, slurry, etc. Preferred detergent additive formulations include granulates, in particular non-dusting granulates, liquids, in particular stabilized liquids, or slurries.

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multiple compartments. It can be of any form, shape and material which is suitable for hold the composition, e.g., without allowing the release of the composition from the pouch prior to water contact. The pouch is made from water soluble film which encloses an inner volume. The inner volume can be divided into compartments of the pouch. Preferred films are polymeric materials, preferably polymers which are formed into a film or sheet. Preferred polymers, copolymers or derivates thereof are selected from polyacrylates, and water-soluble acrylate copolymers, methyl cellulose, carboxy methyl cellulose, sodium dextrin, ethyl cellulose, hydroxyethyl cellulose, hydroxypropyl methyl cellulose, maltodextrin, polymethacrylates, most preferably polyvinyl alcohol copolymers and hydroxypropyl methyl cellulose (HPMC). Preferably the level of polymer in the film for example PVA is at least about 60%. The preferred average molecular weight will typically be about 20,000 to about 150,000. Films can also be of blend compositions comprising hydrolytically degradable and water-soluble polymer blends such as polylactide and polyvinyl alcohol (known under the Trade reference M8630 as sold by Chris Craft In. Prod. of Gary, Indiana, US) plus plasticizers like glycerol, ethylene glycerol, propylene glycol, sorbitol and mixtures thereof. The pouches can comprise a solid laundry detergent composition or part components and/or a liquid cleaning composition or part components separated by the water-soluble film. The compartment for liquid components can be different in composition than compartments containing solids. See, e.g., US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent which is not unit dosed may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e., if a solid object (e.g., laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants, e.g., anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g., a two-stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

Enzymes in the form of granules, comprising an enzyme-containing core and optionally one or more coatings, are commonly used in granular (powder) detergents. Various methods for preparing the core are well-known in the art and include, for example, a) spray drying of a liquid enzyme-containing solution, b) production of layered products with an enzyme coated as a layer around a pre-formed inert core particle, e.g. using a fluid bed apparatus, c) absorbing an enzyme onto and/or into the surface of a pre-formed core, d) extrusion of an enzyme-containing paste, e) suspending an enzyme-containing powder in molten wax and atomization to result in prilled products, f) mixer granulation by adding an enzyme-containing liquid to a dry powder composition of granulation components, g) size reduction of enzyme-containing cores by milling or crushing of larger particles, pellets, etc., and h) fluid bed granulation. The enzyme-containing cores may be dried, e.g. using a fluid bed drier or other known methods for drying granules in the feed or enzyme industry, to result in a water content of typically 0.1-10% w/w water.

The enzyme-containing cores are optionally provided with a coating to improve storage stability and/or to reduce dust formation. One type of coating that is often used for enzyme granulates for detergents is a salt coating, typically an inorganic salt coating, which may e.g. be applied as a solution of the salt using a fluid bed. Other coating materials that may be used are, for example, polyethylene glycol (PEG), methyl hydroxy-propyl cellulose (MHPC) and polyvinyl alcohol (PVA). The granules may contain more than one coating, for example a salt coating followed by an additional coating of a material such as PEG, MHPC or PVA.

For further information on enzyme granules and production thereof, see WO 2013/007594 as well as e.g. WO 2009/092699, EP 1705241, EP 1382668, WO 2007/001262, U.S. Pat. No. 6,472,364, WO 2004/074419 and WO 2009/102854.

Uses

The present invention is also directed to methods for using the subtilase variants according to the invention or compositions thereof in laundering of textile and fabrics, such as household laundry washing and industrial laundry washing.

The invention is also directed to methods for using the variants according to the invention or compositions thereof in cleaning hard surfaces such as floors, tables, walls, roofs etc. as well as surfaces of hard objects such as cars (car wash) and dishes (dish wash).

The subtilase variants of the present invention may be added to and thus become a component of a detergent composition. Thus, one aspect of the invention relates to the use of a subtilase variant in a cleaning process such as laundering and/or hard surface cleaning.

A detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The cleaning process or the textile care process may for example be a laundry process, a dishwashing process or cleaning of hard surfaces such as bathroom tiles, floors, table tops, drains, sinks and washbasins. Laundry processes can for example be household laundering, but may also be industrial laundering. Furthermore, the invention relates to a process for laundering of fabrics and/or garments, where the process comprises treating fabrics with a washing solution containing a detergent composition and at least one protease variant of the invention. The cleaning process or a textile care process can for example be carried out in a machine washing process or in a manual washing process. The washing solution can for example be an aqueous washing solution containing a detergent composition.

The last few years there has been an increasing interest in replacing components in detergents that are derived from petrochemicals with renewable biological components such as enzymes and polypeptides without compromising the wash performance. When the components of detergent compositions change, new enzyme activities or new enzymes having alternative and/or improved properties compared to the previously used detergent enzymes such as proteases, lipases and amylases may be needed to achieve a similar or improved wash performance when compared to the traditional detergent compositions.

The invention further concerns the use of subtilase variants of the invention in a proteinaceous stain removing process. The proteinaceous stains may be stains such as food stains, e.g., baby food, cocoa, egg or milk, or other stains such as sebum blood, ink or grass, or a combination hereof.

Washing Method

The present invention relates to a method of cleaning a fabric, a dishware or hard surface with a detergent composition comprising a protease variant of the invention.

A preferred embodiment concerns a method of cleaning, the method comprising the steps of: contacting an object with a detergent composition comprising a protease variant of the invention under conditions suitable for cleaning the object. In a preferred embodiment the detergent composition is used in a laundry or a dish wash process.

Still another embodiment relates to a method for removing stains from fabric or dishware which comprises contacting the fabric or dishware with a composition comprising a protease of the invention under conditions suitable for cleaning the object. In the method of cleaning of the invention, the object being cleaned may be any suitable object such as a textile or a hard surface such as dishware or a floor, table, wall, etc.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The detergent compositions of the present invention are suited for use in laundry and hard surface applications, including dish wash. Accordingly, the present invention includes a method for laundering a fabric or washing dishware. The method comprises the steps of contacting the fabric/dishware to be cleaned with a solution comprising the detergent composition according to the invention. The fabric may comprise any fabric capable of being laundered in normal consumer use conditions. The dishware may comprise any dishware such as crockery, cutlery, ceramics, plastics such as melamine, metals, china, glass and acrylics. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

The enzyme(s) of the detergent composition of the invention may be stabilized using conventional stabilizing agents and protease inhibitors, e.g., a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or Cl2 or SSI. The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In some preferred embodiments, the detergent compositions provided herein are typically formulated such that, during use in aqueous cleaning operations, the wash water has a pH of from about 5.0 to about 12.5, or in alternative embodiments from about 5.0 to about 11.5, or in alternative embodiments, even from about 6.0 to about 10.5. In some preferred embodiments, granular or liquid laundry products are formulated to have a pH from about 6 to about 8. Techniques for controlling pH at recommended usage levels include the use of buffers, alkalis, acids, etc., and are well known to those skilled in the art.

The present invention is further described by the following examples that should not be construed as limiting the scope of the invention.

EXAMPLES

Example 1: Preparation of Polypeptides

Mutation and introduction of expression cassettes into *Bacillus subtilis* was performed by standard methods known in the art. All DNA manipulations were performed by PCR (e.g. as described by Sambrook et al.; *Molecular Cloning*; Cold Spring Harbor Laboratory Press) using standard methods known to the skilled person.

Recombinant *B. subtilis* constructs encoding subtilase polypeptides were inoculated into and cultivated in a complex medium (TBgly) under antibiotic selection for 24 h at 37° C. Shake flasks containing a rich media (PS-1: 100 g/L Sucrose (Danisco cat. no. 109-0429), 40 g/L crust soy (soy bean flour), 10 g/L $Na_2HPO_4.12H_2O$ (Merck cat. no. 106579), 0.1 ml/L Dowfax63N10 (Dow) were inoculated in a ratio of 1:100 with the overnight culture. Shake flask cultivation was performed for 4 days at 30° C. shaking at 270 rpm.

Recombinant *B. subtilis* colonies encoding subtilase polypeptides were transferred into and cultivated in a complex medium (TBgly) under antibiotic selection for 24 h at 37° C. 24-Well deep well plates containing 3 ml TBgly were inoculated 1:100 with overnight culture. Cultivation was performed for 4 days at 30° C. with agitation at 220 rpm. For harvest, cells were sedimented by centrifugation and the supernatant was sterilized using 0.2 μm 96-well filter plates (Pall Corporation).

Example 2: Storage Stability Assay I—Stability of Variants in Culture Supernatants Proteolytic activity can be determined by a method employing Suc-AAPF-PNA as the substrate. Suc-AAPF-PNA, or Suc-Ala-Ala-Pro-Phe-pNA, is an abbreviation for N-Succinyl-Alanine-Alanine-Proline-Phenylalanine-p-Nitroanilide, and is a blocked peptide which can be cleaved by endoproteases. Following cleavage, a free PNA molecule is liberated which has a yellow color and thus can be measured by visible spectrophotometry at wavelength 405 nm.

Sterile filtered culture supernatants of variants of the invention prepared as described above were tested undiluted and diluted 1:1 with 0.01% Triton X-100. For each variant, 2 wells with each concentration were included. 30 µl protease sample was mixed with 270 µl Model A liquid detergent (see Table 1 below) in the well of a microtiter plate (detergent plate, Nunc U96 PP 0.5 ml) using a magnetic bar (on a Zephyr pipetting station (Caliper LifeSciences) for 30 min). 20 µl of this mixture was then transferred to another microtiter plate and mixed with 150 µl 0.1 M Tris pH 8.6. 30 µl of this dilution was transferred to a new microtiter plate, and after addition of 70 µl substrate solution (0.72 mg/ml Suc-Ala-Ala-Pro-Phe-pNA (Bachem L-1400) in 0.1 M Tris pH 8.6) the activity of the unstressed sample was determined from the initial slope of the increase in measured absorbance at 405 nm (measured every 20 sec for 5 min on a Spectra-Max Plus instrument). After sealing, the detergent plate was incubated at 40° C. in an Eppendorf Thermomixer (no shaking). After 3-4 and 21-23 hours incubation, samples of 20 µl were withdrawn and residual activity of the samples stressed by detergent and heat was measured as with the initial unstressed activity.

The decrease in protease activity during incubation with detergent was assumed to be exponential. Half-lives (T½) were calculated from linear regression of Log(Activity) versus incubation time, and half-life improvement factors (T½ IF) were calculated as the half-life of protease variant relative to the half-life of the wild-type BPN' protease (SEQ ID NO: 1) as the reference.

Table 2 below provides the half-life improvement factor for variants of the invention having the indicated mutations compared to the wild-type BPN' protease with SEQ ID NO: 1. It may be seen that all of the tested variants provide an improved half-life in the detergent compared to the wild-type protease.

TABLE 1

Composition of Model A detergent

| Ingredient | Content of active component (% w/w) |
| --- | --- |
| (C10-C13) alkylbenzene sulfonic acid | 11.6 |
| Sodium lauryl ether sulfate | 4.9 |
| Soy fatty acid | 2.8 |
| Coco fatty acid | 2.8 |
| Alcohol ethoxylate | 11.0 |
| Sodium hydroxide | 1.8 |
| Ethanol | 2.7 |
| Propane-2-ol | 0.3 |
| Propane-1,2-diol | 6.0 |
| Glycerol | 1.7 |
| Triethanolamine | 3.3 |
| Sodium formate | 1.0 |
| Sodium citrate | 2.0 |
| DTMPA-Na7 | 0.2 |
| Copoly(acrylic acid/maleic acid), sodium salt | 0.18 |
| Phenoxyethanol | 0.5 |
| Water | |

TABLE 2

Storage Stability. T½ IF: Half-life improvement factor relative to SEQ ID NO: 1

| Mutations | T½ IF |
| --- | --- |
| S63G Q206L L209W G215A A216V Y217L | 5.0 |
| S63G S204D L209W G215A Y217L | 4.9 |
| S63G N76D L209W G215A Y217L | 4.5 |
| N76D Y104V G128S G131* N212G | 4.0 |
| S9E S63G L209W G215A Y217L | 3.7 |
| N76D S159E Q206L N212G A216V | 3.2 |

TABLE 2-continued

Storage Stability. T½ IF: Half-life improvement factor relative to SEQ ID NO: 1

| Mutations | T½ IF |
| --- | --- |
| Q206L N212G A216V | 3.1 |
| S63G Q206L L209W G215A Y217L | 3.1 |
| S204D Q206L N212G A216V | 3.0 |
| N76D Y104V G128S G131P | 2.7 |
| S159E Q206L N212G A216V | 2.6 |
| S63G L209W G215A Y217L | 2.5 |
| S9E S159E Q206L A216V | 2.3 |
| S63G Y104V G128S G131* L209W G215A Y217L | 2.2 |
| N76D Y104V G128S G131* | 2.2 |
| S63G Y104V G128S G131P L209W G215A Y217L | 2.1 |
| Y104V G128S G131* Q206L A216V | 2.1 |
| Y104V G128S G131* S159E Q206L A216V | 2.1 |
| N76D Y104V G128S G131P N212G | 2.0 |
| Y104V I107L G128S G131* Q206L | 2.0 |
| N76D N212G F261W Y262E | 1.8 |
| S204D Q206L N212G | 1.8 |
| S9E S204D N212G | 1.8 |
| Y104V G128S G131P Q206L A216V | 1.7 |
| S63G L209W G215A Y217L F261W Y262E | 1.7 |
| Y104V G128S G131P S204D N212G | 1.6 |
| S9E Y104V G128S G131* | 1.6 |
| N76D A88V S204D N212G | 1.5 |
| Y104V G128S G131P S159E Q206L A216V | 1.2 |

Example 3: Storage Stability Assay II—Stability of Purified Variants

Purification may, for example, be performed as follows:

The culture broth is centrifuged at 26000×g for 20 minutes and the supernatant is carefully decanted from the precipitate. The supernatant is filtered through a Nalgene 0.2 µm filtration unit in order to remove the remains of the host cells. The pH in the 0.2 µm filtrate is adjusted to pH 8 with 3 M Tris base and the pH-adjusted filtrate is applied to a MEP Hypercel column (Pall Corporation) equilibrated in 20 mM Tris/HCl, 1 mM $CaCl_2$, pH 8.0. After washing the column with the equilibration buffer, the column is step-eluted with 20 mM $CH_3COOH$/NaOH, 1 mM $CaCl_2$, pH 4.5. Fractions from the column are analyzed for protease activity using the Suc-AAPF-pNA assay at pH 9 and peak fractions are pooled. The pH of the pool from the MEP Hypercel column is adjusted to pH 6 with 20% (v/v) $CH_3COOH$ or 3 M Tris base and the pH-adjusted pool is diluted with deionized water to the same conductivity as 20 mM MES/NaOH, 2 mM $CaCl_2$, pH 6.0. The diluted pool is applied to an SP-Sepharose® Fast Flow column (GE Healthcare) equilibrated in 20 mM MES/NaOH, 2 mM $CaCl_2$, pH 6.0. After washing the column with the equilibration buffer, the protease variant is eluted with a linear NaCl gradient (0→0.5 M) in the same buffer over five column volumes. Fractions from the column are analyzed for protease activity using the Suc-AAPF-pNA assay at pH 9 and active fractions are analyzed by SDS-PAGE. Fractions in which only one band is observed on the Coomassie stained SDS-PAGE gel are pooled as the purified preparation and used for further experiments.

Purified protease variants are diluted with 0.01% Triton X-100 to the same concentration e.g. 0.2 mg/ml, with the concentration calculated e.g. from absorbance at 280 nm. For each protease variant at least 2 wells are tested. 30 µl diluted protease sample is mixed with 270 µl concentrated liquid detergent (e.g. Model A detergent; see the composition of this detergent in Table 1 above) in the well of a microtiter plate (detergent plate, e.g. Nunc U96 PP 0.5 ml) e.g. using a magnetic bar. 20 µl of this mixture is then transferred to another microtiter plate and diluted appropriately with 0.1 M Tris pH 8.6 (where "appropriately" refers to the fact that the dilution should ensure that the initial rate of substrate hydrolysis lies within the linear range of the assay, which persons skilled in the art will readily be able to determine). 30 µl of this dilution is transferred to a new microtiter plate, and after addition of 70 µl substrate solution (e.g. 0.72 mg/ml Suc-Ala-Ala-Pro-Phe-pNA (Bachem L-1400) in 0.1 M Tris pH 8.6) the activity of the unstressed sample is determined from the initial slope of increase in measured absorbance at 405 nm (e.g. measured every 20 sec for 5 min on a SpectraMax Plus instrument). After sealing, the detergent plate is incubated at a suitable temperature (e.g. 40° C.) in an Eppendorf Thermomixer (no shaking). After e.g. 4 and 24 hours incubation, samples of 20 µl are withdrawn and residual activity of stressed samples is measured as with the initial unstressed activity.

The decrease in activity during incubation with detergent is assumed to be exponential. Half-lives (T½) are found from linear regression of Log(Activity) versus incubation time, and half-life improvement factors (T½ IF) are calculated as the half-life of the protease variant relative to the half-life of the reference, where the reference is suitably the BPN' protease having SEQ ID NO: 1.

The invention claimed is:

1. A subtilase variant, comprising mutations at three or more positions selected from position 209 in combination with two or more additional positions selected from the group consisting of positions 63, 215, and 217, wherein positions are numbered according to SEQ ID NO: 1, wherein the mutation at position 63 is S63G or S63A, the mutation at position 209 is L209W, the mutation at position 215 is G215A and the mutation at position 217 is Y217L, Y217I, Y217V or Y217M and wherein the variant has protease activity and a sequence identity to SEQ ID NO: 1 of at least 85% and less than 100%.

2. The subtilase variant of claim 1, comprising the substitutions S63G, L209W, G215A and Y217L.

3. The subtilase variant of claim 1, further comprising at least one mutation selected from the group consisting of S9E/D, N76D/E, Y104V/I/L/M, G128S/A/T, G131*, G131P, S204D/E, Q206L/I/V/M, A216V/I/L/M, F261W/N/Y and Y262E/D.

4. The subtilase variant of claim 1, comprising one of the following sets of mutations:
S63G L209W G215A Y217L;
S9E S63G L209W G215A Y217L;
S63G N76D L209W G215A Y217L;
S63G S204D L209W G215A Y217L;
S63G Q206L L209W G215A A216V Y217L;
S63G Q206L L209W G215A Y217L;
S63G L209W G215A Y217L F261W Y262E;
S63G Y104V G128S G131* L209W G215A Y217L; or
S63G Y104V G128S G131P L209W G215A Y217L.

5. The subtilase variant of claim 1, wherein the variant has an increased storage stability in a detergent composition compared to the subtilase of SEQ ID NO: 1.

6. A method for stabilizing a subtilase variant, the method comprising introducing into a parent subtilase having protease activity and at least 85% sequence identity to SEQ ID NO: 1 mutations L209W in combination with two or more substitutions selected from S63G/A, G215A and Y217L/I/V/M.

7. The method of claim 6, wherein the stabilized subtilase variant has an increased storage stability in a detergent composition compared to the subtilase of SEQ ID NO: 1.

8. A method for obtaining a subtilase variant, the method comprising
(a) providing a host cell comprising a polynucleotide encoding a variant of a parent protease having three or more mutations, compared to SEQ ID NO: 1, wherein the variant has protease activity and a sequence identity to SEQ ID NO: 1 of at least 85%, and wherein the mutations are L209W in combination with two or more substitutions selected from S63G/A, G215A and Y217L/I/V/M;
(b) cultivating the host cell under conditions suitable for expression of the variant; and
(c) recovering the variant.

9. A detergent composition comprising a subtilase variant according to claim 1 and at least one detergent component, and optionally further comprising at least one additional enzyme.

10. The subtilase variant of claim 1, comprising mutations at one or more additional positions selected from the group consisting of positions 9, 76, 88, 104, 107, 128, 131, 159, 204, 206, 212, 216, 261 and 262, wherein positions are numbered according to SEQ ID NO: 1.

* * * * *